United States Patent [19]

Chang

[11] 4,164,563

[45] Aug. 14, 1979

[54] NON-GREASY COMPOSITIONS

[75] Inventor: Robert W. H. Chang, Shoreview, Minn.

[73] Assignee: Minnesota Mining and Manufacturing Company, St. Paul, Minn.

[21] Appl. No.: 561,421

[22] Filed: Mar. 24, 1975

[51] Int. Cl.$^2$ .......................................... A61K 31/745
[52] U.S. Cl. ...................................... 424/83; 424/177; 424/271
[58] Field of Search .......................... 424/114, 181, 83

[56] References Cited

U.S. PATENT DOCUMENTS

| | | | |
|---|---|---|---|
| 2,628,187 | 2/1953 | Frohmader et al. | 424/83 |
| 2,996,432 | 8/1961 | Modderno | 424/83 |
| 3,029,188 | 4/1962 | Cyr et al. | 424/83 |
| 3,079,299 | 2/1963 | Heilig | 424/83 |
| 3,215,599 | 11/1965 | Thau et al. | 424/83 |
| 3,574,827 | 4/1971 | Beerbower | 424/83 |
| 3,733,403 | 5/1973 | Chen | 424/83 |

FOREIGN PATENT DOCUMENTS

| | | | |
|---|---|---|---|
| 780918 | 8/1957 | United Kingdom | 424/83 |
| 806719 | 12/1958 | United Kingdom | 424/83 |
| 884713 | 12/1961 | United Kingdom | 424/83 |

OTHER PUBLICATIONS

Brevet Special de Medicament No. 3,377M, France, 6/1965.

*Primary Examiner*—Dale R. Ore
*Attorney, Agent, or Firm*—Cruzan Alexander; Donald M. Sell; James V. Lilly

[57] ABSTRACT

Compositions for topical application to skin are provided wherein greasy, occlusive viscous bases are made non-greasy while remaining occlusive. The compositions comprise a mixture of from about 40 to 90%, and preferably from about 60 to 90%, by weight of a greasy viscous base and from about 10 to 60%, and preferably from about 10 to 40%, by weight of a solid, nonirritating ointment forming powder having a number average maximum dimension of less than about 30 microns. Said viscous base is substantially nonabsorbed by said powder at temperatures below about 50° C. Other ingredients such as colorants, consistency modifiers, medicaments, etc. may optionally be added to the compositions.

17 Claims, 1 Drawing Figure

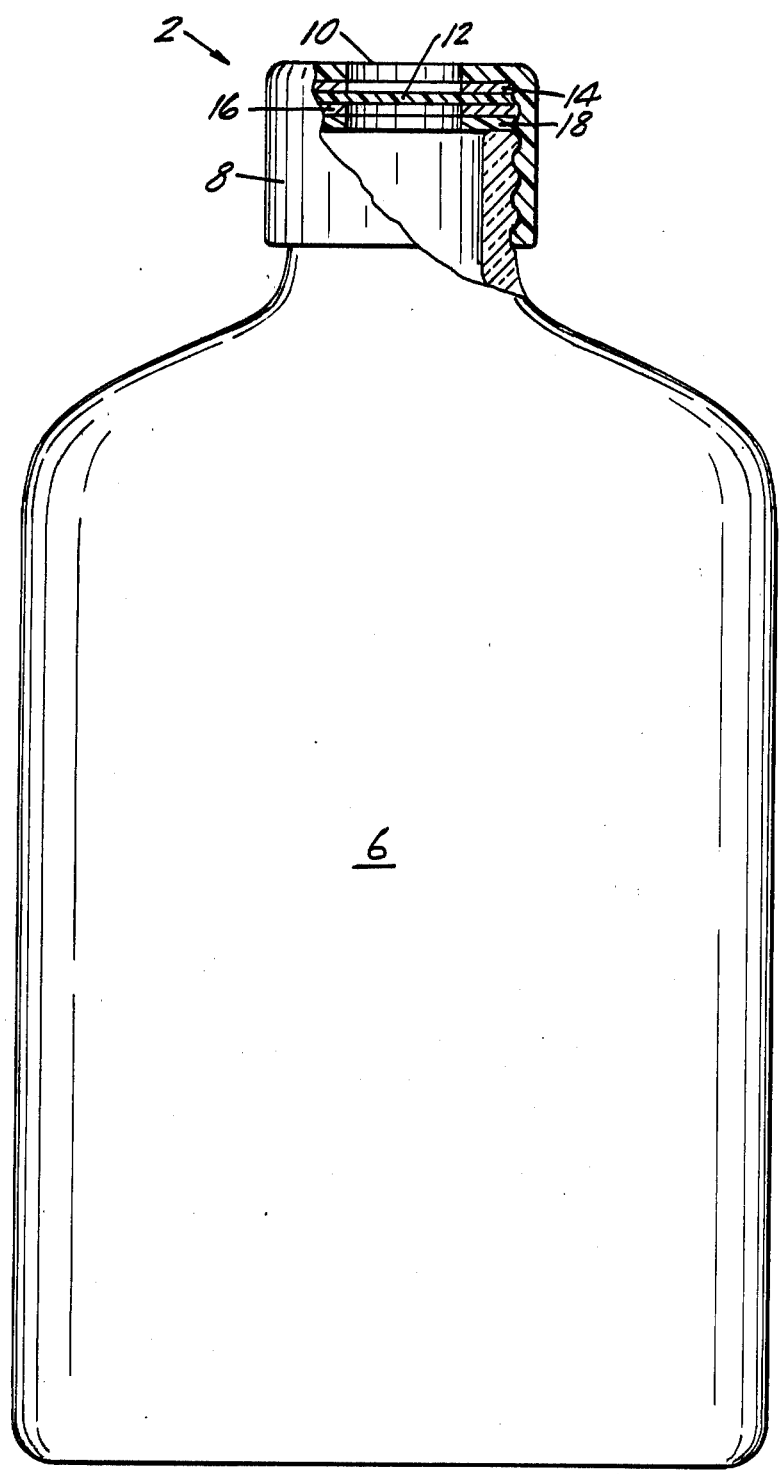

NON-GREASY COMPOSITIONS

This invention relates to compositions for topical application to the skin. More particularly it relates to non-greasy, occlusive compositions for topical application to the skin.

Skin-care products, such as emollient ointments and hand lotions, have been available for years. Many of the ingredients used therein have an oily or greasy nature and consequently impart this same characteristic to the end products. As a result many skin-care products have an aesthetically unpleasant feel and look about them. Additionally they are easily transferred from the location on the skin where they have been applied to furniture, clothing, etc., thereby staining them.

This greasy nature often limits the cosmetic formulator. For example, it may be desirable to increase the concentration of one or more of the greasy ingredients for functional reasons such as improved occlusivity. However, any increase in the amount of these ingredients also serves to increase the aesthetically unpleasant character of the final product thereby giving it low product acceptability and rendering the increase commercially unfeasible.

In order to alleviate these problems, and consequently increase the formulator's flexibility, different avenues of approach have been tried. Early approaches to the problem involved the addition of thickening agents to the emollients. Thus, U.S. Pat. No. 2,627,938 discloses the addition of polyethylene powder to an emollient, such as mineral oil, by dissolving the polyethylene therein at elevated temperatures and then rapidly cooling the resultant solution to a gel. However, products prepared in accordance with this method retain their greasy nature. Moreover, they are syneristic, that is, the emollient separates from the polyethylene upon standing.

U.S. Pat. No. 3,733,403 discloses the addition of from 0.1 to 5% of an anti-syneresis agent to a gel of the type disclosed in U.S. Pat. No. 2,627,938. The anti-syneresis agent comprises a highly porous powdered magnesium silicate having a surface area from about 250 to 359 $m^2/g$. While the addition of the anti-syneresis agent does reduce syneresis, the resultant powder still retains its greasy nature. Another approach to the problem is disclosed in U.S. Pat. No. 3,852,475. There a hydrophobic starch is added to petrolatum in order to reduce the greasy appearance and feel normally associated therewith. The hydrophobic starches used are starch esters containing hydrophobic groups and complex ethers of starch. They are not easily swelled by water but will absorb water from the skin without forming a paste.

Still other approaches to the problem involved the addition of compounds that form a dried film over the area of application. Thus, U.S. Pat. No. 3,100,180 discloses the use of fluorine containing elastomers in protective lotions that dry to form a barrier film. U.S. Pat. Nos. 3,214,338 and 3,627,871 disclose the use of water soluble polymers that dry after application to form nontacky films. This type of composition is not entirely satisfactory, however, because it suffers from various disadvantages such as lengthy drying time, dry film peeling and dry film cracking due to inflexibility.

The present invention alleviates these and other disadvantages attendant with the prior art by providing the cosmetic formulator with non-greasy, occlusive, aesthetically pleasing compositions useful as moisturizers, cosmetics, medicament carriers, etc. In accordance with the present invention, there is provided in a greasy, occlusive composition for topical application to the skin comprising a viscous base selected from the group consisting of solid petrolatum, animal oils, mineral oils, and synthetic oils, wherein said oils have been thickened by an agent selected from the group consisting of waxes and hydrocarbon polymers, the improvement comprising forming a non-greasy, occlusive composition by mixing from about 40 to 90%, and preferably from about 60 to 90%, by weight of said non-greasy composition of said viscous base with from about 10 to 60%, and preferably from about 10 to 40%, by weight of said non-greasy composition of a solid, non-irritating ointment forming powder having a number average maximum dimension of less than about 30 microns, said viscous base being substantially nonabsorbed by said powder below about 50° C.

Compositions of the present invention have a low gloss or shine and, therefore, do not appear greasy. As a result they are aesthetically pleasing in appearance. Once applied, noncolored compositions of the present invention are substantially invisible to the eye further adding to their aesthetically pleasing nature. Compositions of the present invention do not substantially transfer from the area of skin where they have been applied to furniture, clothing, etc., and consequently do not stain surrounding objects. Additionally they do not exhibit any syneresis nor do they dry, peel, or crack after they have been applied. Despite possessing these characteristics they unexpectedly exhibit good resistance to removal by incidental water rinsing while being easily removed by simple washing with soap and water even though they are occlusive. Furthermore, compositions of the present invention do not absorb substantial quantities of water from the skin.

Surprisingly the novel compositions of the present invention achieve this balance of desirable properties through the addition of relatively large quantities of a solid, non-irritating, substantially non-absorbent powder. This result was unexpected since the addition of relatively large quantities of such a powder would be expected to result in non-spreadable pastes rather than the highly useful compositions of the present invention.

As they are used throughout the specification the following terms have the following meanings:
  a) Occlusive Composition:
    A composition that reduces moisture vapor transmission through a first porous substrate at specified conditions by at least 30%;
  (b) Non-greasy Composition:
    A composition that transfers less than about 5 mg of material from a second porous substrate to a 4.25 cm diameter "Whatman" No. 4 filter paper under specified conditions.

Methods for determining moisture vapor transmission and material transfer and descriptions of the porous substrates used are set forth below.

Generally the viscous base comprises from about 40 to 90%, and preferably from about 60 to 90%, by weight of the non-greasy composition of the present invention. A variety of compounds may serve as the viscous base. For example, the base may comprise solid petrolatum, or alternatively it may comprise animal oils, mineral oils and synthetic oils that have been thickened by means of a thickening agent.

Solid petrolatum consists of a mixture of hydrocarbons (including mineral oil and microcrystalline hydrocarbon waxes) of such nature that when melted material is cooled to ordinary room temperature (e.g. 25° C.) it congeals to a translucent, apparently amorphous or jelly-like material. Traditionally solid petrolatum has been derived from asphalt-free crude petroleums by removal by distillation of the more volatile fractions to leave an undistilled residue. Accordingly it contained a large amount of oil having a wide range of viscosities and molecular weights and included more or less the relatively coarse crystalline type of paraffin closely resembling or identical with the ordinary paraffin wax of commerce. Recently solid petrolatum has been synthetically prepared by blending mineral oil and microcrystalline waxes or paraffinic waxes or both with the objective of yielding a semisolid mixture of hydrocarbons.

Representative examples of solid petrolatun useful in the present invention include "Vaseline Petroleum Jelly" (commercially available from Cheesebrough-Ponds, Inc., New York, N.Y., a decolorized synthetic blend of mineral oil and microcrystalline wax or paraffin wax or both having a viscosity of 200 SSU or higher at about 30° C. wherein the wax comprises 30% or more by weight); "Aquaphor" (commercially available from Duke Laboratories, South Norwalk, Conn.); and "Plastibase" (commercially available from Squibb, New York, N.Y., a combination of mineral oils and heavy hydrocarbon waxes).

A variety of animal oils, mineral oils, and synthetic oils are useful in the practice of the present invention. They may vary in viscosity from those that are thin liquids to those that do not flow at ordinary temperatures. Preferably they have a viscosity in the range of from about 5 to 100 centipoise at about 25° C. and are non-irritating to the skin.

Representative examples of animal oils useful in the present invention include mixtures of acetylated lanolin alcohols such as "Acetulan" (commercially available from American Cholesterol Products, Edison, N.J., viscosity about 10 Centipoise [cps] at about 25° C., specific gravity from about 0.85 to about 0.88 at about 25° C.); mixtures of fatty acids such as "Emulan" (commercially available from Emulin, Inc., Kenosha, Wis., an oil of mink, viscosity about 50 cps at about 29° C., specific gravity of from about 0.90 to 0.92). Lanolin may also be used as the viscous base of the present invention.

Representative examples of mineral oils useful in the present invention includes mixtures of heavy liquid petroleum hydrocarbons such as "Nujol" (commercially available from Plough, Inc., Memphis, Tenn., viscosity of about 65 cps at about 25° C.); and light mineral oils such as "Drakeol" #5 (commercially available from Pennsylvania Refining Co., Butler, Pa., viscosity of about 7 cps at about 25° C.).

Representative examples of synthetic oils useful in the present invention include isopropyl myristate; oleyl myristate; methyl, isopropyl and butyl esters of fatty acids and acetoglyceride esters.

A preferred class of oils for use in the present invention are the mineral oils. Heavy mineral oils are particularly preferred when a high degree of occlusivity is desired while light mineral oils are preferred when a high degree of medicament release is desired.

A variety of compounds have been found useful in thickening animal, mineral and synthetic oils before converting them to non-greasy compositions. Generally these compounds comprise from about 4 to about 12% by weight of the non-greasy composition and are selected from the group consisting of substantially saturated aliphatic monomeric compounds having a minimum of twelve carbon atoms per molecule and polyolefins. The thickening agents are solid at room temperature (e.g. 25° C.) and absorb the oils when heated to about 50° C.–150° C. in the presence thereof. The amount of thickening agent used may, of course, be varied. The exact amount chosen is dependent upon the viscosity of the oil or other viscous base to be thickened, the molecular weight of the thickening agent and the final product desired.

It is preferred that the thickening agent be partially crystalline and partially amorphous. Although the exact method by which it operates is not known it is believed that the crystalline portion of the thickening agent does not absorb the oil when heated therewith at elevated temperatures (e.g. above 50° C.) while the amorphous portion of the thickening agent does absorb the oil when heated therewith at elevated temperatures. As a result the crystalline portion does not swell thereby maintaining the integrity of the agent while the amorphous portion does swell. Upon cooling to less than about 50° C., the swollen amorphous portion retains and, consequently, thickens the viscous base.

Representative examples of substantially saturated aliphatic monomeric compounds useful as thickening agents in the present invention include cetyl alcohol, stearic acid, cholesterol, glycerol monostearate, etc. Other thickening agents of the type described may also be used.

Polyolefins useful as thickening agents in the present invention have from 2 to 6 carbon atoms in the recurring unit. Representative examples of useful polyolefins include polyethylene, polypropylene, polybutylene, polymethylbutylene and copolymers of olefins and acetates such as ethylene-vinyl acetate copolymers (e.g. "Microthene" FE-532 commercially available from U.S.I. Chemical Co., New York, N.Y.). A preferred thickening agent is polyethylene. A particularly preferred polyethylene is "Epolene" C-14 (commercially available from Eastman Chemical Co., Kingsport, Tenn.).

The thickening agent is preferably combined with a small amount (e.g. from about 0.3 to about 0.5% by weight of the oil) of an unvulcanized, amorphous elastomeric block copolymer. The block copolymer is composed of terminal glassy resinous polymer blocks and a central elastomeric polymer block wherein each glassy or resinous terminal group has a glass transition temperature above room temperature (e.g. 25° C.) and an average molecular weight of between about 2,000 and 100,000. The terminal groups constitute approximately 15 percent of the total block copolymer weight. The elastomeric block is a conjugated diene having a glass transition temperature below that of the terminal groups. A particularly useful amorphous unvulcanized elastomeric block copolymer is "Kraton" 1107 (commercially available from the Shell Chemical Co., New York, N.Y.). In this copolymer the terminal glassy or resinous polymer blocks are styrene blocks and the central elastomeric copolymer block is an isoprene block.

A variety of compounds have been found useful in rendering viscous bases non-greasy. In general, such compounds, hereinafter referred to as ointment powders, are solid at room temperature (i.e. 25° C.), have a number average maximum dimension of less than about 30 microns and are preferably non-irritating to human skin. The ointment powders do not absorb the viscous base at temperatures below about 50° C., but rather, they render viscous bases non-greasy by absorbing the viscous base at said temperatures. They comprise from about 10 to 60%, and preferably from about 10 to 40, by weight of the nongreasy composition. They may be organic or inorganic compounds. Additionally, they may be of any configuration although spherical powders are preferred.

Useful organic ointment powders include the same class of polyolefins that is useful as thickening agents. However, combining a thickening portion of these polyolefins with an ointment forming portion and then adding that combination to an oil during the thickening step (described below) does not result in the novel compositions of the present invention because a high viscosity (e.g. 100,000 cps or more) gel results that is both greasy and nonspreadable. If the combination is added during the ointment forming step (also described below) a high viscosity (e.g. 100,000 cps or more) non-spreadable paste results. Consequently, the thickening portion of these polyolefins must be added during the thickening step and the ointment forming portion of these polyolefins must be added during the ointment forming step.

Polyolefin ointment powders useful in compositions of the present invention have from 2 to 6 carbon atoms in the recurring unit and a molecular weight in the range of from about 3,000 to about 150,000. Representative examples of such polyolefin powders include "Microthene" FN-510 (commercially available from U.S.I. Chemical Co., New York, N.Y., a spherical polyethylene powder, molecular weight 140,000, density of about 0.924, melt index of about 5 gm. 10 min., number average maximum dimension of about 20 microns); "Microthene" FA-520 (commercially available from U.S.I. Chemical Co., New York, N.Y., a spherical polyethylene powder, density of about 0.962, melt index of about 17 gm/10 min., number average maximum dimension of less than 20 microns); "Epolene" C-14 (commercially available from Eastman Chemical Co., Kingsport, Tenn., a polyethylene powder, molecular weight of about 23,000, density of about 0.918, melt index of about 1.6 gm/10 min.); "Microthene" FE-532 (commercially available from U.S.I. Chemical Co., New York, N.Y., an ethylene-vinyl acetate copolymer, density of about 0.928, melt index of about 9 gm/10 min., number average maximum particle size of 30 microns). A preferred organic ointment powder is polyethylene. A particlarly preferred polyethylene powder is "Epolene" C-14.

Useful inorganic powders include the insoluble silicates such as hydrated magnesium and aluminum silicates. Hydrated magnesium silicate, also known as talc, is a very fine, odorless crystalline powder that varies in color from white to grayish white. Hydrated aluminum silicate, also known as bentonite, is a very fine, crystalline powder that varies in color from cream to pale brown.

The handleability of compositions of the present invention may be, and preferably is, improved by the addition of consistency modifiers that may comprise from about 8 to about 50 percent by weight of the non-greasy composition. The consistency modifiers may be solid or liquid at room temperature (e.g. 25° C.), do not dissolve the thickening agent or the ointment powder at room temperature, and are non-irritating to the skin.

Useful consistency modifiers include the animal and synthetic oils that are also useful as a portion of the viscous base. Other useful consistency modifiers include monofunctional alcohols having from about 3 to 16 carbon atoms such as propyl alcohol, octyl alcohol; polyfunctional alcohols such as propylene glycol, butylene glycol, glycerol, dipropylene glycol, polyethylene glycol, and polypropylene glycol; and liquid esters of dicarboxcyclic acids such as triethylene glycol diethyl butyrate, di(2-ethyhexyl) adipate, and glycerol monostearate. A small amount of water, preferably deionized water, may also be used as a consistency modifier. Still other useful consistency modifiers are oil soluble fatty acid polypeptide condensates prepared by the reaction of fatty acids and collagen. One such polypeptide condensate is "Crotein IP" (commercially available from Croda, Inc., New York, N.Y.).

The consistency modifiers may be used by themselves or in combination with each other. A preferred combination of consistency modifiers comprises a blend of about 34% by weight oil soluble fatty acid polypeptide condensate; 16.5% by weight acetylated lanolin alcohols; 16.5% by weight liquid lanolin; 16.5% by weight cetyl alcohol and 16.5% by weight deionized water.

Consistency modifiers may be added directly to the oil used in the viscous base prior to thickening or, alternatively, they may be added after thickening. Addition before thickening has the effect of reducing the concentration of a given amount of thickening agent thereby reducing its effect. This in turn necessitates the addition of more thickening agent to achieve a given result. However, either method results in satisfactory product.

Other ingredients may be added to compositions of the present invention. For example, colorants such as pigments and dyes may be added to make blemish hiding cosmetics, eye shadows, etc. Medicaments such as keratolytic aids, corticosteroids, antibiotics (e.g. bacitracin, neomycin sulfate, polymycin B sulfate), etc. may also be added to make medicinal compositions wherein the medicaments are capable of being released therefrom.

The compositions of the present invention may be prepared in a variety of ways. For example, they may be prepared by dissolving a thickening agent in solid petrolatum or in oil. Generally it is not necessary to thicken solid petrolatum. In any event, thickening is accomplished by heating the ingredients to from about 50° C.-150° C., and preferably from 100° C.-130° C., with simple agitation until the appearance of the solution changes from cloudy to clear. The solution is then cooled to less than about 50° C. to form a thickened viscous base. As the rate of cooling is not critical to the practice of the present invention, any heat exchange method may be used. The thickened viscous base is then made non-greasy by simply admixing a modifying portion of an ointment powder to produce a uniform non-greasy occlusive composition. Typically, admixtue of ointment powder is carried out at temperatures less than about 50° C. in any equipment that results in its intimate blending with the viscous base (e.g. a three-roll mill). Alternatively compositions of the present invention may be prepared by simply admixing a modifying portion of an ointment powder into solid petrolatum. Other ingredients (e.g. colorants, medicaments, etc.) may be added either before or after the viscous base has been rendered non-greasy.

The exact method of preparation is, of course, a matter of choice and is influenced by such factors as the viscosity of the base to be made non-greasy, the consistency desired in the finished composition, etc. It is understood that more than one viscous base, thickener, etc. may be employed in compositions of the present invention.

The compositions of the present invention may be provided as ointments, creams, or lotions. Creams and lotions are prepared by a variety of well-known techniques such as emulsion-type preparation. In an emulsion-type preparation a non-greasy ointment (e.g. a non-greasy composition containing less than about 20% water by weight) is combined with an emulsifying agent such as triethanolamine stearate, and an extending aid such as water under conditions of high shear such that an emulsion of the non-greasy ointment in the extending aid is established. Other ingredients such as buffering agents, opacifying agents, fragrances, and preservatives may also be included.

A procedure for measuring the occlusivity of various compositions was developed that was not subject to the variability of human skin. Occlusivity was determined by first measuring the amount of water lost through a first standard porous substrate having no occluding aid applied thereto (the control) and then determining the amount of water lost through the substrate after a thin layer of occluding aid had been applied thereto. The amount of water lost was reported in terms of moisture vapor transmission (MVT) and was calculated according to the formula:

$$MVT = W/AT$$

wherein W was the weight of water lost (in milligrams), A was the area available for vapor transmission (in square centimeters) and T was the time during which vapor transmission was determined (in hours).

Percent occlusivity (% Occ) was then calculated from the formula:

$$\%Occ = 100 [1 - (MVT_s/MVT_c)]$$

where $MVT_s$ and $MVT_c$ were the moisture vapor transmission through occluded substrate and the control, respectively.

Reference is now made to the FIGURE in order to assist in more fully describing the test method. The FIGURE is a perspective view in elevation of a test apparatus 2 with a section of the cover cut away to show an opening of predetermined area through which moisture vapor may pass and a combination of gaskets and a first standard porous substrate.

MVT of the control was measured by placing a known about of water (50-60 gm) into a 4 oz. )0.12 liter) flint glass jar 6. A metal cover 8 for the jar 6 having a 1 in. (2.5 cm) diameter hole 10 cut into its center was provided. A section of a first porous substrate 12 was attached to an aluminium gasket 14 also having a 1 in. (2.5 cm) diameter hole cut into its center. The substrate 12 covered the mouth of the jar 6. A brass gasket 16 and a cured polychloroprene gasket 18 that has a 1 inch (2.5 cm) diameter hole cut into their centers were also provided. The gasket 18, the gasket 16, the substrate 12 and the gasket 14 respectively were placed over the mouth of the jar 6 and the cover 8 was then tightened hand tight. The resultant apparatus 2 had a total area of 4.9 square centimeters available for moisture vapor transmission. The apparatus 2 and its contents were conditioned by placing them into a test chamber for from 6 to 24 hours. The chamber was maintained at 54% relative humidity, 73.5° F. (23° C.) and had an air flow of 50-80 ft./min. (16-30 m/min.) through it. The apparatus 2 was removed after conditioning, weighed and returned to the test chamber for another 24 hours. The apparatus 2 was then removed again and weighed. The amount of water lost between weighings was calculated and used to determine the MVT of the control.

MVT of the test material was measured according to the above procedure except that the material to be tested was applied to the substrate 12 with a fingertip and then adjusted to a 2 mil (50.8 micron) thickness prior to placing the substrate 12 over the gasket 16 by means of a "Multiple-Clearance Film Applicator", Model 34, made by Precision Gauge and Tool Company. The gasket 14 was then placed over the occluded substrate 12 and the cover 8 was tightened hand tight. Occlusivity was then determined using the above-described formula.

In all tests for measuring MVT, the substrate 12 comprised a porous 5 mil( 127 microns) thick polyurethane film. It was prepared by mixing the following ingredients together to form a paste:

| | |
|---|---|
| "Estane" 5707-F1* | 14.31 grams |
| Dimethyl Formamide | 59.53 grams |
| Sodium Chloride (50% 5-10 microns) | 25.89 grams |
| Light Brown Sienna Pigment** | 0.05 grams |
| Dark Brown Umber Pigment*** | 0.25 grams |

*Polyurethane resin solution, 15% total solids, 670–1290 centipoise viscosity, specific gravity of 1.20, tensil strength of 8000 psi (5624 kg/cm$^2$), modulus at 300 percent elongation of 4000 psi (2812 kg/cm$^2$), commercially available from B. F. Goodrich Chemical Co., Cleveland Ohio.
**Commercially available as "Sienna Cosmetic Dye" #2673 (nonaniline) from Kohnstamm H. and Co., New York, New York.
***Commercially available as "Umber Cosmetic Dye" #1985 (nonaniline) from Kohnstamm H. and Co., New York, New York.

The resultant paste was knife coated onto a polypropylene carrier to a width of 25 in. (62.5 cm) and a thickness of about 12 mil (304.8 microns). The coated web was passed through a water bath to leech out the sodium chloride and dimethyl formamide and then dried to a continuous porous film by passing it through an air circulating oven maintained at 121° C. at a rate of 3 ft./min. (0.9 m/min.). When used for MVT determination, the film was removed from the carrier, cut to the proper size, and placed over the mouth of the jar 6.

A procedure for measuring non-greasiness of various compositions was developed whereby the amount of material that transferred from a second porous substrate to a "Whatman" No. 4 filter paper was measured. Material transfer was measured by spreading the material to be tested over a 5 cm × 8 cm area of 5 mil. (125 micron) thick second porous substrate. A 2 mil (50 micron) layer of test material was obtained by means of a "Multiple-Clearance Film Applicator", Model 34 commercially available able from Precision Gauge and Tool Co. A "Whatman" No. 4 filter paper (4.25 cm diameter) was weighed and then placed on the test material. A 100 gm weight was placed upon the filter paper for 60 seconds. The weight and paper were then removed and the weight and paper reweighed. The amount of test material which had transferred to the weight and paper was determined by the weight increase.

The second porous substrate was prepared by milling the following ingredients together on a two-roll mill:

| | |
|---|---|
| "Estane" 5707-F1 | 87.25 grams |
| Calcium Carbonate | 153.25 grams |
| Calcium Stearate | 2.2 grams |
| "Paraplex" G-62** | 4.175 grams |
| Light Brown Sienna Pigment | 1.25 grams |

-continued

| | |
|---|---|
| Dark Brown Umber Pigment | 1.875 grams |

*A polyurethane resin commercially available from B. F. Goodrich Chemical Co., Cleveland, Ohio. It is derived from 1.00 mole poly(1,4-butylene adipate) glycol, 1.85 moles 1,4 butane diol and 2.85 moles diphenylmethane-p,p'-diisocyanate.
**A high molecular weight (about 1000) epoxidized oil plasticizer having an acid number of 0.4 mg KOH/gm, and a saponification number of 182 mg KOH/gm, commercially available from Rohm & Haas, Philadelphia, Pennsylvania.

The milled product was ground into a powder then extruded to form a 10 mil±2 mils (250 micron ±50 microns) film. A 3:1 uniaxial stretch orientation reduced the caliper to 5 mils ±1 mil (125 microns ±25 microns).

The following examples are meant to further illustrate, but not limit, the invention. Parts and percentages are by weight unless otherwise specified. In the examples, the materials listed below are referred to by their trademark or tradenames. The list contains the composition and manufactures of those materials.

(1) "Nujol"
  A mixture of heavy liquid petroleum hydrocarbons
  Viscosity of 65 cps at 25° C.
  Plough, Inc., Memphis, Tennessee
(2) "Kraton" 1107
  Amorphous elastomeric block copolymer having central isoprene blocks and terminal styrene blocks
  Shell Chemical Co., New York, N.Y.
(3) "Epolene" C-14
  Polyethylene powder
  Density: 0.918 gm/cm$^3$
  Molecular weight: 23,000
  Melt index: 1.6 gm/10 min.
  Eastman Chemical Co., Kingsport, Tennessee
(4) "Microthene" FN-510
  Polyethylene powder (spherical)
  Density: 0.924 gm/cm$^3$
  Particle size: 20 micron (number average)
  Molecular weight: 140,000
  Melt index: 5 gm/10 min.
  U.S.I. Chemical Co., New York, New York
(5) "Drakeol" 5
  Light mineral oil having a viscosity of 7 cps at 25° C.
  Pennsylvania Refining Company, Butler Pa.
(6) "Acetulan"
  A mixture of acetylated lanolin alcohols
  Viscosity: 10 cps at 25° C.
  Specific gravity: 0.85–0.88
  Hydroxyl No. : 8 max.
  Acid No. : 1 max
  American Cholesterol Products, Edison, N.J.
(7) "Crotein IP"
  liquid oil soluble fatty acid polypeptide condensate
  Specific gravity: 0.88–0.89
  Acid value: 180–200
  Croda, Inc., New York, N.Y.
(8) "Vaseline"
  Decolorized synthetically prepared solid petrolatun comprising a blend of mineral oil and microcrystalline wax or paraffin wax or both wherein the wax comprises at least 30% by weight
  Cheesebrough Ponds, Inc., New York N.Y.
(9) "Aquaphor"
  A yellowish, greasy, occlusive ointment
  Duke Laboratories, South Norwalk, Conn.
(10) "Plastibase"
  A combination of mineral oils and heavy hydrocarbon waxes having a molecular weight of about 1300, the large proportion of which are liquid
  Squibb, New York, N.Y.

EXAMPLE 1

A greasy viscous base consisting of 17.9 grams of "Nujol" and 0.1 grams of "Kraton" 1107 was prepared by heating the ingredients for four hours at 130° C. with constant stirring until the solution became clear. "Epolene" C-14 (2 grams) was then dissolved in the "Nujol"/"Kraton" solution by heating the ingredients to 130° C. for four fours. The resulting solution was cooled to a thickened greasy viscous base by placing it in a room temperature (e.g. 25° C.) environment. One half of the thickened greasy viscous base was converted into uniform non-greasy, occulsive composition by simple admixture of varying amounts of an ointment powder ("Microthene " FN-510) therewith at room temperature. The greasy viscous base and the non-greasy compositions were then tested for percent occulsivity and greasiness. The compositions made and the results obtained are given in Table I.

TABLE I

| | Compositions | | | | | |
|---|---|---|---|---|---|---|
| | A | B | C | D | E | F |
| Viscous Base (Parts) | 100 | 90 | 80 | 70 | 65 | 60 |
| Ointment Powder (Parts) | 0 | 10 | 20 | 30 | 35 | 40 |
| % Occ. | 95.9 | 97.9 | 96.5 | 95.2 | 96.8 | 91.2 |
| Greasiness (mg) | 6.7 | 2.6 | 2.7 | 1.1 | 0.6 | 0.7 |

EXAMPLE 2

Non-greasy, occulsive compositions were prepared in accordance with Example 1 except that varying amounts of hydrated magnesium silicate (talc) were used as the ointment powder. The non-greasy compositions were then tested for percent occlusivity and non-greasiness. The compositions made and the results obtained are given in Table II.

TABLE II

| | Compositions | | | | |
|---|---|---|---|---|---|
| | G | G | I | J | K |
| Viscous Base (Parts) | 90 | 80 | 70 | 65 | 60 |
| Ointment Powder (Parts) | 10 | 20 | 30 | 35 | 40 |
| % Occ. | 97.8 | 97.1 | 92.6 | 85.4 | 78.9 |
| Greasiness (mg) | 4.9 | 2.3 | 1.9 | 1.6 | 1.5 |

EXAMPLE 3

A greasy viscous base and a non-greasy, occulsive composition were prepared as described in Example 1, Composition D except that "Drakeol" #5 was substituted for the "Nujol". The greasy viscous base and the non-greasy composition were tested for percent occlusivity and greasiness. The results are given in Table III.

TABLE III

| | Greasy Viscous Base | Non-Greasy Composition |
|---|---|---|
| % Occ | 91.9 | 82.1 |
| Greasiness (mg) | 14.1 | 4.1 |

EXAMPLE 4

A thickened greasy viscous base was prepared as described in Example 1, except that 2 grams of "Microthene" FN-510 were used in place of 2 grams of "Epolene" C-14 in thickening the greasy viscous base. One half of the greasy viscous base was converted into a uniform non-greasy occulsive composition as described in Example 1, Composition F.

A mixture of consistency modifiers consisting of 0.44 grams "Acetulan", 0.44 grams liquid lanolin, and 0.44 grams cetyl alcohol was prepared by mixing the ingredients together at 71° C. until the cetyl alcohol had melted.

A consistency modified, non-greasy, occulsive composition was then prepared by mixing the non-greasy composition with 0.88 grams of "Crotein IP" at room temperature (e.g. 25° C.) followed by mixing the mixture of consistency modifiers into the composition at 60°–70° C. until a uniform product resulted. The composition was cooled to room temperature (e.g. 25° C.) and 0.44 grams of deionized water were mixed therewith at room temperature until a uniform product was obtained.

The greasy viscous base and the consistency modified non-greasy composition were then tested for percent occlusivity and greasiness. The results are given in Table IV.

TABLE IV

|  | Greasy Viscous Base | Non-Greasy Composition |
|---|---|---|
| % Occ | 96.8 | 93.8 |
| Greasiness (mg) | 6.7 | 2.8 |

EXAMPLE 5

Greasy viscous bases and occlusive, non-greasy compositions were prepared. Two solutions, one consisting of 18 grams of isopropyl myristate (IPM) and 2 grams of "Epolene" C-14 and the other consisting of 18 grams of "Acetulan" and 2 grams of "Epolene" C-14 were prepared by heating the ingredients at 130° C. for four hours. The solutions were then cooled to thickened, greasy viscous bases by placing them in a room temperature (e.g. 25° C.) environment. One half of each thickened, greasy viscous base was converted into a uniform non-greasy occlusive composition by mixing 4.3 grams of "Microthene" FN-510 therewith. The compositions were then tested for percent occlusivity and greasiness. The results of these tests are given in Table V.

perature (e.g. 25° C.) until a uniform composition resulted.

Six grams of "Aquaphor" and six grams of "Plastibase" were also converted to occlusive, non-greasy compositions according to this procedure by mixing four grams of "Microthene" FN-510 therewith until a uniform composition resulted. The unmodified "Vaseline", "Aquaphor", and "Plastibase" and the non-greasy compositions were tested for percent occlusivity and greasiness. The results of these tests are given in Table VI.

TABLE VI

|  | "Vaseline" | | "Aquaphor" | | "Plastibase" | |
|---|---|---|---|---|---|---|
|  | Unmodified Greasy Composition | Non-Greasy Composition | Unmodified Greasy Composition | Non-Greasy Composition | Unmodified Greasy Composition | Non-Greasy Composition |
| % Occ | 97.3 | 97.7 | 94.6 | 94.1 | 95.5 | 98.2 |
| Greasiness (mg) | 10.4 | 2.6 | 17.1 | 2.8 | 22.4 | 2.4 |

EXAMPLE 7

A viscous base consisting of 17.9 grams of "Drakeol" #5 and 0.1 grams of "Kraton" 1107 was prepared by heating the ingredients for four hours at 130° C. with constant stirring until the solution became clear. "Microthene" FN-510 (2 grams) was then dissolved in the "Drakeol"/"Kraton" solution by heating the ingredients at 130° C. for four hours. The resulting solution was then cooled to room temperature (e.g. 25° C.) by placing it into a bath of acetone and dry ice. The resultant product, a thickened, greasy viscous base, was made into a non-greasy medicament by the addition of 12 grams of "Microthene" FN-510, 3 grams of propylene glycol and 0.033 grams of dexamethasone-t-butyl acetate (a steroid). The ingredients were mixed together on a 3 roll paint mill until a uniform, non-greasy product was obtained.

The release of the steroid from the ointment through occluded hairless mouse skins was measured according to the procedure described by Fritsch ans Stoughton, J. Invest. Dermatol 41, 307(1963). Two samples were run. Seventy milligrams (mg) of the medicament was applied to each mouse skin. After 24 hours, an average of 1.72 mg (2.44%) of the steroid had been released.

EXAMPLE 8

A greasy viscous base consisting of 58.7 grams of "Drakeol" #5 and 0.3 grams of "Kraton" 1107 was prepared by heating the ingredients for four hours at 130° C. with constant stirring until the solution became clear. "Microthene" FN-510 (6.5 grams) was then dissolved in the "Drakeol"/"Kraton" solution by heating

TABLE V

|  | IPM | | "Acetulan" | |
|---|---|---|---|---|
|  | Greasy Viscous Base | Non-Greasy Composition | Greasy Viscous Base | Non-Greasy Composition |
| % Occ | 52.6 | 32.2 | 61.2 | 44.8 |
| Greasiness (mg) | 6.6 | 3.1 | 9.0 | 1.6 |

EXAMPLE 6

Six and one-half grams of "Vaseline" were converted to an occlusive, non-greasy composition by mixing 3.5 grams of "Microthene" FN-510 therewith at room temthe ingredients at 130° C. for four hours. The resulting solution was then cooled by placing it into a bath of acetone and dry ice for 15 minutes. The resultant product, a thickened, greasy, viscous base was made into a non-greasy medicament by the addition of 32.8 grams of "Microthene" FN-510, 0.962 grams of Bacitracin, 0.5 grams of neomycin sulfate, 0.061 grams of polymyxin B sulfate, 0.1 gram methyl-para-hydroxy benzoate and 0.1 gram 2-n-propyl-para-hydroxy benzoate. The ingredients were mixed together on a 3 roll paint mill until a uniform, non-greasy product was obtained. Microbiological activity of the formulation was determined by the method described in 38 Fed. Reg.19817 (1973). The results of these tests are given in Table VII.

TABLE VII

| Temp. of Test | Length of Test | Antibiotic Released | | |
|---|---|---|---|---|
| | | Bacitracin | Neomycin Sulfate | Polymyxin B Sulfate |
| 45° C. | 2 wks | 0.16–0.19g | 0.31–0.46g | 0.058–0.097g |
| 37° C. | 4 wks | 0.18–0.19g | 0.33–0.52g | 0.045–0.073g |
| 0° C. | 6 mos | 0.17–0.19g | 0.38–0.56g | 0.040–0.045g |
| 60° C. | 2 wks | 0.13–0.17g | 0.36–0.56g | 0.056–0.061g |
| RT | 4 wks | 0.13–0.22g | 0.35–0.56g | 0.34–0.048g |

What is claimed is:

1. A non-greasy occlusive composition for topical application to the skin comprising from about 40 to 90 percent by weight of a greasy viscous base, and from about 10 to 60 percent by weight of a solid, non irritating ointment-forming powder; wherein said viscous base is selected from the group consisting of solid petrolatum, animal oils, mineral oils, and synthetic oils, wherein said oils have been thickened by an agent selected from the group consisting of waxes and hydrocarbon polymers; and wherein said ointment forming powder comprises a polyolefin having from 2 to 6 carbon atoms in the recurring unit, a molecular weight of from about 3,000 to 150,000 and a number average maximum dimension of less than about 30 microns, said viscous base being substantially non-absorbed by said ointment-forming powder below about 50° C., and wherein said greasy viscous base is mixed with said ointment-forming powder at a temperature of less than about 50° C.

2. A composition according to claim 1 wherein said ointment-forming powder is polyethylene.

3. A composition according to claim 2 wherein said oil comprises a mineral oil having a viscosity of from about 7 to 65 centipoise at 25° C.

4. A composition according to claim 3 wherein said thickening agent comprises a polyolefin having from 2 to 6 carbon atoms in the recurring unit, and wherein said thickening agent comprises from about 4 to 12 percent by weight of said non-greasy composition.

5. A composition according to claim 4 wherein said thickening agent is polyethylene.

6. A composition according to claim 1 containing a medicament.

7. A composition according to claim 6 wherein the medicament is selected from the group consisting of steriod, bacitracin, neomycin sulfate and polymyxin B sulfate.

8. A composition according to claim 1 in the form of an ointment.

9. A composition according to claim 1 in the form of a lotion.

10. A composition according to claim 1 in the form of a cream.

11. A non-greasy, occlusive composition for topical application to skin comprising from about 40 to 90 percent by weight of a greasy viscous base, from about 10 to 60 percent by weight of a solid, non-irritating ointment-forming powder, and from about 8 to 50 percent by weight of a consistency modifier; wherein said viscous base comprises an oil selected from the group consisting of animal, mineral, and synthetic oils, said oils having been thickened by an agent selected from the group consisting of substantially saturated, aliphatic monomeric compounds having at least 12 carbon atoms per molecule and polyolefins, and said ointment-forming powder comprises a polyolefin having from 2 to 6 carbon atoms in the recurring unit and a molecular weignt in the range of from about 3,000 to 150,000 and has a number average maximum dimension of less than about 30 microns, said viscous base being substantially non-absorbed by said ointment-forming powder below about 50° C.; and wherein said greasy viscous base is mixed with said ointment-forming powder at a temperature of less than about 50° C.

12. A composition according to claim 11 wherein said ointment-forming powder is polyethylene.

13. A composition according to claim 12 wherein said oil comprises a mineral oil having a viscosity of from about 5 to 100 centipoise at 25° C.

14. A composition according to claim 13 wherein said polyolefin thickening agent is polyethylene.

15. A composition according to claim 14 wherein there is combined with said thickening agent from about 0.3 to 0.5 percent by weight of said viscous base of an amorphous, elastomeric, unvulcanized block copolymer composed of terminal styrene blocks having a glass transition temperature above about 25° C. and an average molecular weight of between about 2,000 and 100,000 and a central isoprene block having a glass transition temperature below that of the terminal blocks.

16. A composition according to claim 15 wherein said consistency modifier comprises a blend of 34 percent by weight oil soluble fatty acid polypeptide condensate, 16.5 percent by weight acetylated lanolin alcohols, 16.5 percent by weight liquid lanolin, 16.5 percent by weight cetyl alcohol, and 16.5 percent by weight deionized water.

17. A composition according to claim 11 wherein said substantially saturated aliphatic monomeric thickening agent is cholesterol.

* * * * *

UNITED STATES PATENT AND TRADEMARK OFFICE
CERTIFICATE OF CORRECTION

PATENT NO. : 4,164,563
DATED : August 14, 1979
INVENTOR(S) : ROBERT W. H. CHANG

It is certified that error appears in the above-identified patent and that said Letters Patent are hereby corrected as shown below:

Col. 5, line 4, "absorbing" should read --adsorbing--;

Col. 10, line 40, "G" second occurrence should read --H--.

Signed and Sealed this

Twenty-fifth Day of December 1979

[SEAL]

Attest:

SIDNEY A. DIAMOND

Attesting Officer

Commissioner of Patents and Trademarks